(12) United States Patent
Müller et al.

(10) Patent No.: US 7,406,345 B2
(45) Date of Patent: Jul. 29, 2008

(54) APPARATUS FOR MEASURING AN ANALYTE CONCENTRATION FROM AN OCULAR FLUID

(75) Inventors: Achim Müller, Grossostheim (DE); Roland Schmieder, Aschaffenburg (DE); Klaus Haberstroh, Bodman-Ludwigshafen (DE)

(73) Assignee: Eyesense AG, Basel (CH)

( * ) Notice: Subject to any disclaimer, the term of this patent is extended or adjusted under 35 U.S.C. 154(b) by 188 days.

(21) Appl. No.: 10/545,220

(22) PCT Filed: Feb. 13, 2004

(86) PCT No.: PCT/EP2004/001367

§ 371 (c)(1),
(2), (4) Date: Aug. 10, 2005

(87) PCT Pub. No.: WO2004/071287

PCT Pub. Date: Aug. 26, 2004

(65) Prior Publication Data

US 2006/0155179 A1 Jul. 13, 2006

(30) Foreign Application Priority Data

Feb. 14, 2003 (EP) .................................. 03003381

(51) Int. Cl.
*A61B 5/1455* (2006.01)
(52) U.S. Cl. ................. 600/321; 600/318; 600/319
(58) Field of Classification Search ................. 600/318, 600/319, 320, 321
See application file for complete search history.

(56) References Cited

U.S. PATENT DOCUMENTS

| | | | |
|---|---|---|---|
| 6,088,606 A | 7/2000 | Ignotz et al. | 600/316 |
| 2003/0076508 A1* | 4/2003 | Cornsweet | 356/517 |

FOREIGN PATENT DOCUMENTS

| | | |
|---|---|---|
| GB | 2 373 044 | 9/2002 |
| WO | WO 02/087429 | 11/2002 |

* cited by examiner

*Primary Examiner*—Eric F. Winakur
*Assistant Examiner*—Etsub D Berhanu
(74) *Attorney, Agent, or Firm*—Foley & Lardner LLP

(57) ABSTRACT

The present invention relates to a hand-held fluorescence photometer and method for measuring an analyte level, preferably a blood glucose level, from an ocular fluid. The photometer is based on a dual beams measuring system and it is capable of defining the correct positioning for the measurement. Only when the apparatus is correctly positioned the actual analyte measurement automatically takes place.

12 Claims, 4 Drawing Sheets

APPARATUS FOR MEASURING AN ANALYTE CONCENTRATION FROM AN OCULAR FLUID

This application is a national stage filing under 35 U.S.C. 371 of International Application No. PCT/EP2004/0013677 filed Feb. 13, 2004, which claims benefits under 35 U.S.C. 119(a)-(d) or 365(b) of European Patent Application No. 03003381.5 filed Feb. 14, 2003.

The present invention relates to a hand-held fluorescence photometer and methods for measuring an analyte level, preferably a blood glucose level, from an ocular fluid. The photometer is capable of self defining the correct position with respect to the eye for measuring. As the apparatus is properly positioned the analyte measurement automatically takes place.

One important aspect in the treatment of diabetes is the tight control of blood glucose levels, which requires frequent monitoring of blood glucose levels of patients so as to manage food intake and the dosage and timing of insulin injection. Currently, millions of diabetics are forced to draw blood daily to determine their blood sugar levels. To alleviate the constant discomfort and inconvenience of these individuals, substantial effort has been expanded in the search for a non-invasive or minimally invasive technology to accurately determine blood glucose levels.

Various non-invasive or minimally invasive technologies to measure blood glucose levels from an ocular fluid such as tears, aqueous humor, or interstitial fluid have been described. Relevant to the present invention is the ocular sensor for glucose disclosed in WO-A-01/13783. The ocular sensor described by WO-A-01/13783 is an ophthalmic lens comprising a glucose receptor labeled with a first fluorescent label and a glucose competitor labeled with a second fluorescent label. The two fluorescent labels are selected in a way that while the competitor is bound to the receptor, the fluorescence of the second fluorescent label is quenched via a fluorescence resonance energy transfer. By monitoring the change of the fluorescence intensity at a wavelength around the peak of the fluorescence of the quenchable fluorescent label, the amount of the fluorescently labeled competitor that is displaced from the receptor by glucose is measured and provides a means of determining the glucose concentration in an ocular fluid. This measurement can, in turn, be manipulated to provide a measurement of blood glucose level.

Advantageously, the first fluorescent label could serve as an internal standard in the determination of glucose concentration in an ocular fluid and thereby could enhance the accuracy of determination of glucose concentration in an ocular fluid.

WO-A-02/087429 discloses a fluorescence photometer for measuring blood glucose level from an ocular fluid which is capable of measuring simultaneously two fluorescence intensities at two different wavelengths and that could therefore benefit from the measurement system disclosed in WO-A-01/13783.

However the problem of this technology is its high price and complexity for positioning the measurement tool with respect to the eye of the patient. The positioning of the measurement beam must be done with an accuracy of a few micrometers. While this is perhaps possible with a static measuring system, this is so far impossible with respect to an in vivo measurement assembly with an hand-held apparatus. Therefore there is the need to develop an apparatus for measuring glucose concentration in ocular fluids which is also capable of self defining the correct position for measuring, with an accuracy of a few micrometers. Moreover the measurement on the eye surface with a hand-held fluorescence photometer requires a concept ensuring that only the fluorescence of the ocular fluid or the contact lens but not the background fluorescence of the underlying tissue is measured.

The term "ocular analyte concentration" or "ocular analyte level" as used herein refers to an analyte concentration in an ocular fluid.

The term "blood analyte concentration or level" or "ocular analyte level" as used herein refers to an analyte concentration in the blood stream of a person.

The present invention, in one aspect, provides a hand-held fluorescence photometer for measuring an analyte level, preferably a blood glucose level from an ocular fluid based on a dual beam measuring system having preferably confocal optical paths.

The fluorescence photometer of the invention comprises:
(a) at least a first irradiating means for providing a pilot beam when in use, wherein said pilot beam is irradiated onto the eye of a user from outside the cornea of the eye to excite the pupil fluorescence or first fluorescence wherein said pupil fluorescence travels along a first optical path;
(b) a first detecting means located on the first optical path for detecting the intensity of the pupil fluorescence within the given wavelength range;
(c) a second irradiating means for providing a measurement beam when in use, wherein said measurement beam is irradiated onto the eye of a user from outside the cornea of the eye to excite an ocular analyte sensor, wherein said ocular analyte sensor is in contact with an ocular fluid and upon irradiation with said irradiating means emits a total fluorescence having at least a second fluorescence wavelength band, wherein said second fluorescence travels along a second optical path;
(d) a second detecting means located on the second optical path for detecting the intensity of the second fluorescence at the given wavelength;
wherein, when the fluorescence photometer is in use, said pilot beam is positioned at a fixed angle and distance from the measurement beam, and said angle being greater than 0 degrees and smaller than 90 degrees.

The proper positioning of the apparatus is achieved by measuring the pupil fluorescence intensity, also addressed as first fluorescence intensity, by means of the pilot beam optical path. The intensity of the pupil fluorescence is in fact correlated to the distance of the measurement tool from the eye.

Only when the distance of the measurement tool from the eye is such that the measurement beam irradiates the iris, the actual measurement starts. The iris has an auto fluorescence which is about 100 times lower than the fluorescence of the pupil. Therefore in order to achieve a high signal/noise ratio it is advantageous to direct the measurement beam to hit the iris of the patient's eye. Whenever the photometer is misplaced the measurement beam automatically stops.

The small dimensions together with the high accuracy achieved by the photometer of the present invention allows for the first time to focus two beams at the same time in a patient's eye and therefore to benefit from a dual beam measurement system.

The photometer further includes a calculating means or a processing circuit for determining based on the measured fluorescence intensities:
(a) a distance between the photometer and the patient's eye;
(b) an ocular analyte concentration in the ocular fluid of the user according to a predetermined calibration table or calibration curve;

and an arithmetic means for converting the ocular analyte concentration determined by the calculating means into a blood analyte concentration by referring to a predetermined correlation between blood analyte concentrations and ocular analyte concentrations.

In another aspect, this invention provides a method for measuring an analyte level, preferably blood glucose level from an ocular fluid. Such a method comprises:

(a) providing an ocular analyte sensor in contact with the tear fluid;
(b) providing a hand-held fluorescence photometer in front of the patient's eye, wherein in use said photometer provides a pilot beam and a measurement beam;
(c) irradiating a pilot beam onto the eye of a user from outside the cornea of the eye to excite the pupil fluorescence or first fluorescence wherein said first fluorescence travels along a first optical path;
(d) detecting the intensity of the first fluorescence within the given wavelength range;
(e) correlating the intensity of the pupil fluorescence to the distance of the fluorescence photometer to the eye and thereby determining the exact position of the fluorescence photometer for the measurement; once the exact position has been reached
(f) irradiating a measurement beam onto the eye of a user from outside the cornea of the eye to excite the ocular analyte sensor, wherein said ocular analyte sensor emits a total fluorescence having at least a second fluorescence wavelength band upon irradiation with said irradiating means;
(g) detecting the intensity of the second fluorescence at the given wavelength;
(h) correlating said intensity of the second fluorescence to the analyte level.

In a preferred embodiment the geometry of said fluorescence photometer is such that when the fluorescence photometer is in use, the pilot beam is positioned to a fixed angle and distance from the measurement beam wherein said angle is greater than 0 degrees and smaller than 90 degrees; and the measurement beam is irradiated onto the iris of the patient's eye.

FIGURES

DETAILED DESCRIPTION OF THE INVENTION

Figure 1:
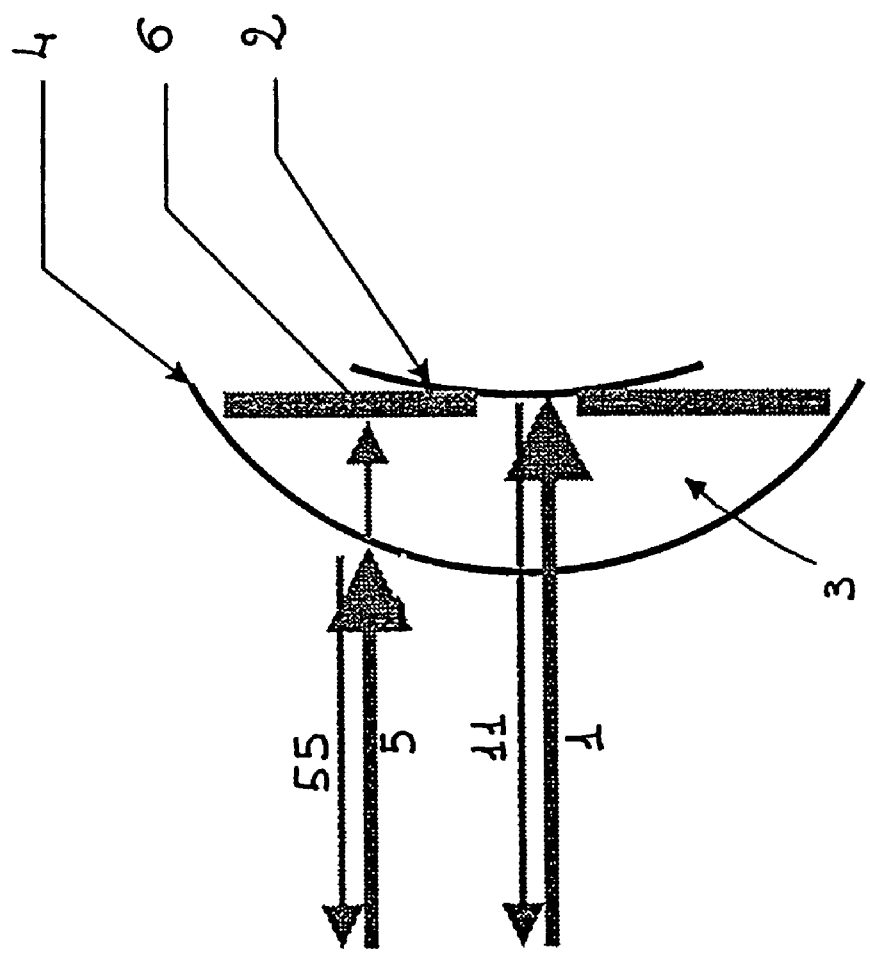
FIG. 1 shows the basic principle of the measurement system according to the present invention.

The basic principle of the measurement system of the present invention is shown in FIG. 1. First, a pilot beam 1 having a well defined wavelength number irradiates the pupil 2 of a patient's eye 3 wearing an ocular analyte sensor (not shown). Such irradiation causes the pupil 2 to emit a first fluorescence 11 of a defined wavelength range which travels along a first optical path and is measured by means of a detector. The measured fluorescence intensity range is then correlated to the distance between the fluorescence photometer and the eye.

Figure 2:
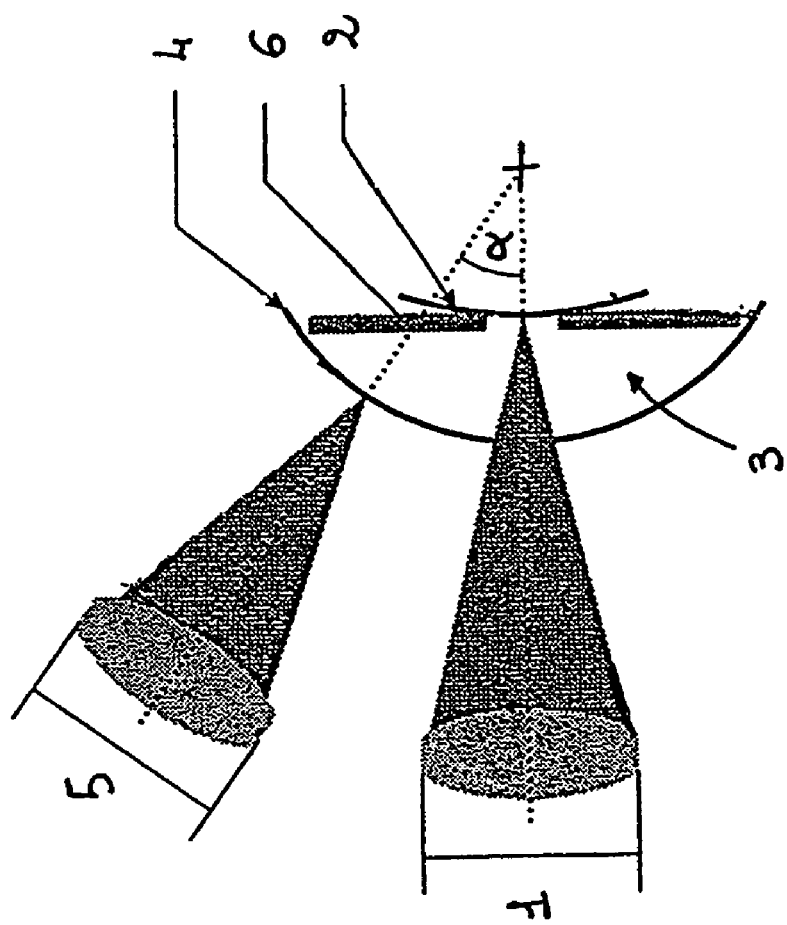
FIG. 2 shows the schematic arrangement of the positioning of the measurement beam and of the pilot beam with respect to a patient's eye.

The geometry of the present fluorescence photometer is such that the pilot beam 1 and a measurement 5 beam which is used for the actual analyte measurement are positioned to a fixed angle α with respect to the patient's eye 3 as shown in FIG. 2. When the distance of the photometer from the eye is such that according to the present geometry the measurement beam irradiates the iris 6 of the patient, an internal circuit (not shown) sends a signal to start the actual analyte measurement. Only then, the measurement beam 5 irradiates the iris 6 of the patient's eye 3. Upon irradiation, the ocular analyte sensor emits a total fluorescence 55 having at least a second wavelength band which travels along a second optical path and is measured by means of a detector. The measured fluorescence intensity is then correlated to the analyte concentration in the blood of the patient.

The angle α is chosen in such a way that the measurement beam irradiates the surface eye in the iris 6 with the limits set by the pupil 2 and the sclera depending on the optics of the photometer and on the optimal distance of measurement. The angle α is greater than 0 degrees and smaller than 90 degrees. Preferably, the angle α is between 20 and 50 degrees and more preferably is between 30 and 40 degrees. A preferred measurement distance is between 100 mm and 1 mm, more preferably is between 5 and 30 mm.

The pilot beam 1 also causes the emission of fluorescence of the ocular sensor but such a fluorescence can be neglected compared to the fluorescence emitted by the pupil 2. Analogously, the measurement beam 5 causes the iris 6 to emit a fluorescence however such a fluorescence may be neglected compared to the fluorescence generated by the ocular glucose sensor.

Advantageously when the pilot beam irradiates the pupil 2 of the patient's eye 3, the pupil itself 2 becomes smaller making the measurement system independent from the pupil 2 versus iris 6 dimensions which may vary from patient to patient and on illumination conditions.

Figure 3:
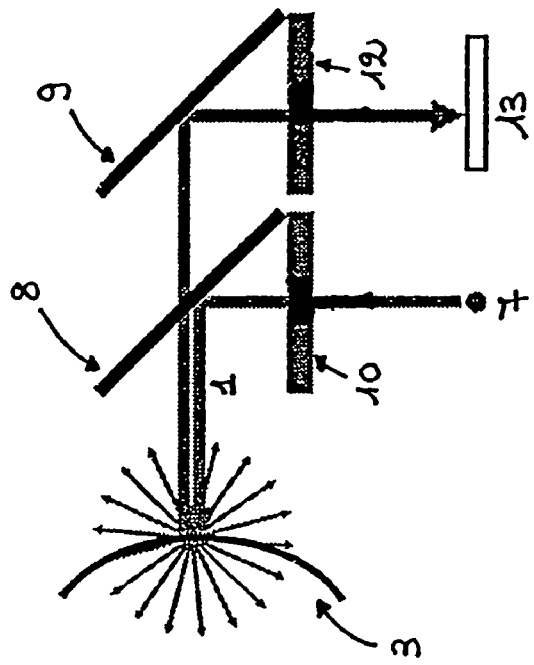
FIG. 3 shows the optical path of the pilot beam in a preferred embodiment of the present invention.

FIG. 3 describes schematically the optical path with respect to the eye of the pilot beam 1 (also shown in FIG. 5) in the fluorescence photometer of a preferred embodiment. Such a fluorescence photometer comprises a first light emitting diode 7 serving as irradiating means, dichroic mirrors 8, 9 with the dual function of reflecting and splitting the beam, filters 10, 12 and a first detecting means 13.

The first light emitting diode 7 emits excitation light of a defined wavelength range which travels trough filter 10 to obtain a monochromatic beam or pilot beam. Dichroic mirror 8 directs the measurement beam towards the patient's eye 3. Before hitting the pupil 2 of the patient's eye 3 the pilot beam 1 is collimated and properly focused by means of standard lenses (not shown). Such irradiation in the eye 3 causes the pupil 2 to emit a characteristic fluorescence also referred as first fluorescence which travels back to the dichroic mirror 8. Then, the dichroic mirror 8 blocks the reflected excitation light and allows the pupil fluorescence, which has a higher wavelength band to proceed further on its optical path. The dichroic mirror 9 directs the pupil fluorescence to filter 12 which makes sure that only the pupil fluorescence having a well defined wavelength range reaches the detector 13 and is measured.

Figure 4:
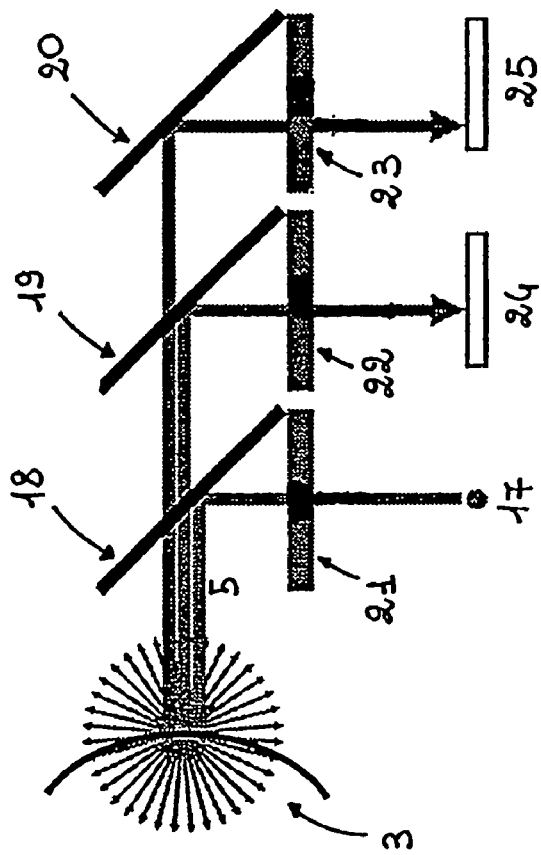
FIG. 4 shows the optical path of the measurement beam in a preferred embodiment of the present invention.

FIG. 4 shows schematically the optical path with respect to the patient's eye 3 of the measurement beam 5 in the fluorescence photometer in a preferred embodiment of the present invention. In this particular embodiment an ocular glucose sensor which emits a total fluorescence having a second fluorescence and a third fluorescence at well defined wavelength numbers is used.

The apparatus comprises at least a second light emitting diode 17 serving as irradiating means, dichroic mirrors 18, 19 with the dual function of reflecting and splitting the beam, a simple mirror 20, filters 21, 22, 23, a second and a third detecting means 24, 25. The second light emitting diode 17 emits excitation light of a defined wavelength range which travels trough filter 21 to obtain a monochromatic beam or measurement beam 5. The dichroic mirror 18 directs the measurement beam 5 towards the patient's eye 3. Before hitting the iris 6 of the patient's eye 3 the measurement beam 5 is collimated and properly focused by means of standard lenses (not shown). Such irradiation of the iris 6 causes the glucose ocular sensor to emit a total fluorescence which travels back to the dichroic mirror 18. Then, the dichroic mirror 18 blocks the reflected excitation light and allows the total fluorescence which has higher wavelength bands to proceed further on its optical path. The dichroic mirror 19 splits the total fluorescence into a second fluorescence having a second wavelength band and a third fluorescence having a third wavelength band. The second fluorescence which has a lower wavelength band is then deviated to filter 22 and the third fluorescence is allowed to pass trough. Filter 22 allows only the second fluorescence with a well defined wavelength number to reach the second detector 24.

The third fluorescence band on its optical path encounters mirror 20 which directs it to the third detector 25 after being filtered out. The third fluorescence having a well defined wavelength number is then measured.

Figure 5:
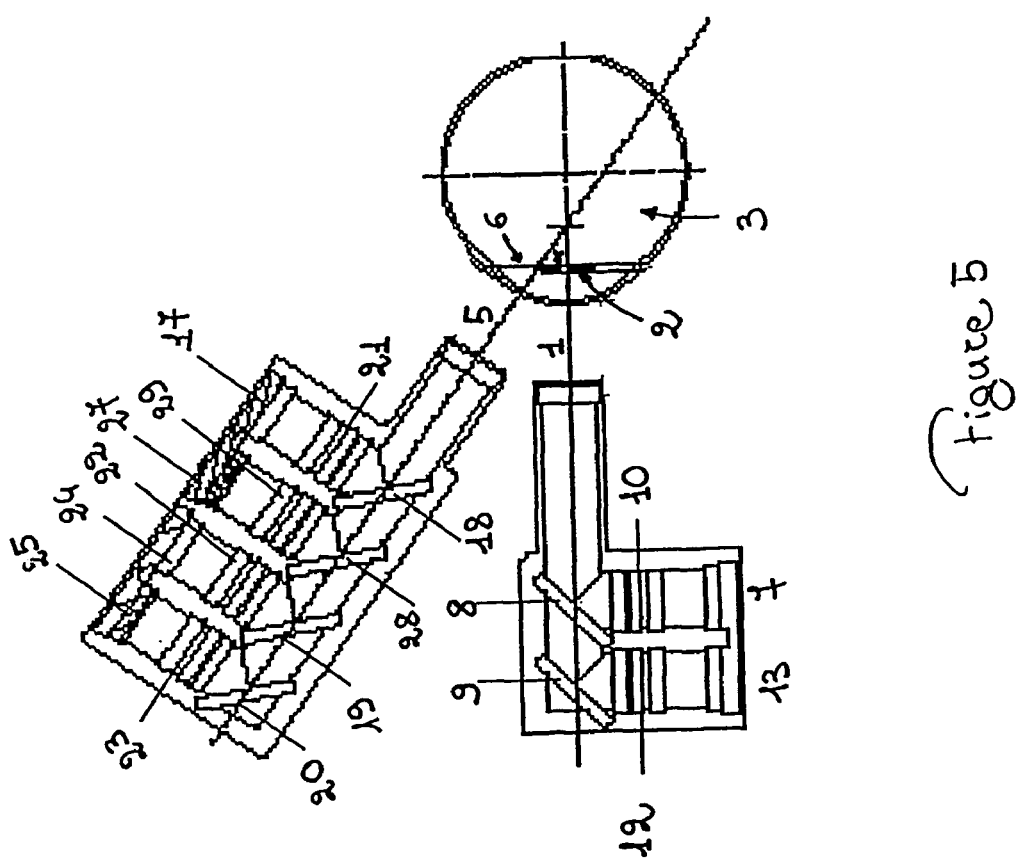
FIG. 5 illustrates the combined optical path of the measurement beam and of the pilot beam with respect to a patient's eye in a particular embodiment of the present invention.

In a particularly preferred embodiment the measurement beam optical path comprises more than one light source. An example of this preferred embodiment is illustrated in FIG. 5 wherein the measurement beam optical path further comprises a third light emitting diode 27, an additional dichroic mirror 28 and an additional filter 29. The excitation light coming from the second light emitting diode 17 is used to excite especially the second fluorescence of the ocular sensor and the third light emitting diode 27 is used to excite especially the third fluorescence of the ocular sensor. In the same manner of the dichroic mirrors described earlier, dichroic mirror 28 blocks lower wavelength number and allows the higher wavelength number band to continue in the optical path.

In a further preferred embodiment the photometer of the present invention further comprises one or more additional irradiating means for providing the pilot beam. The light sources then are preferably used in sequence during the positioning of the apparatus and the measurement.

FIG. 5 also shows a possible combination of the preferred optical path of the pilot beam 1 and of the measurement beam 5 in the fluorescence photometer of the present invention.

The photometer preferably further includes a calculating means or a processing circuit (not shown) for determining based on the measured fluorescence intensities:

(a) a distance between the photometer and the patient's eye;
(b) an ocular glucose concentration in the ocular fluid of the user according to a predetermined calibration table or calibration curve;

and an arithmetic means for converting the ocular glucose concentration determined by the calculating means into a blood glucose concentration by referring to a predetermined correlation between blood glucose concentrations and ocular glucose concentrations. The present invention, in a further aspect, provides kits for calibrating an apparatus for measuring ocular glucose concentrations;

and a light-emitting display panel serving as means for displays the blood glucose concentrations.

To a person skilled in the art it will appear obvious to modify the apparatus described above in the case in which the ocular sensor emits a fluorescence with only one wavelength band or in the case in which the ocular sensor emits a fluorescence with more than two wavelength bands. For example, the number of dichroic mirrors in the measurement beam optical path may be diminished or increased. Analogously the number of light source may be on convenience increased.

The analyte to be measured may be glucose as well as any other substance present in an ocular fluid such as hormones. The fluorescence photometer then has to be modified accordingly within the concept of the invention. For example, both the dichroic mirror and filter positions with respect to the measurement and/or pilot beam optical path have to be optimized depending on the ocular analyte sensor and on the optics employed.

The light sources are preferably Surface Mounted Device light emitting diodes having a defined wavelength range which are characterized by uniform light distribution and smaller power compared to standard light emitting diodes. In alternative, any other kind of light emitting diodes, lasers or electroluminescence light sources could be employed.

Dichroic mirrors block lower wavelength number and allow the higher wavelength number band to continue in the optical path. Their positioning with respect to the beams optical path as well as the filter positioning as to be optimized for every specific case measurement system.

In a preferred embodiment wherein the ocular glucose sensor emits a second fluorescence at 520 nm and a third fluorescence at 590 nm, a surface mounted light emitting diode having an excitation light of 465 nm is used. The dichroic mirrors and the filters preferably have an angle of 45 and 90 degree respectively with respect to the pilot beam and measurement beam optical paths. The angle $\alpha$ between the pilot beam and the measurement beam in this preferred embodiment is 35 degrees.

The photometer to make these measurements could take several configurations such as a moderate sized laboratory instrument or a small hand-held, portable, self contained unit suitable for the user to carry easily in a pocket or purse. For example, the length of the fluorescence photometer is preferably between 3 and 20 cm, preferably between 5 and 15 cm and most preferably between 7 and 10 cm. The thickness is, for example, between 1 and 7 cm, preferably, between 2 and 4 cm. The instrument is used by looking into an optical window while holding the apparatus in front of the eye to a distance which is determined by the pilot beam 1 when the instrument is in use. Preferably an integral cover is provided to protect the optical elements. A display preferably using liquid crystals or light emitting diodes, which provides readout of the analyte value and instrument diagnostic including battery status is position in the internal surface of such a cover 31. In alternative the display is positioned on an external cover. A battery compartment is provided at the opposite end of the instrument.

To cope with the small dimensions of the photometer the pilot beam as well as measurement beam preferably have confocal optics. To accurately position the photometer with respect to the patient's eye it is advantageous that the pilot beam has a sharp focus. To diminish the effect of eye movement during the glucose measurement the measurement beam preferably has a more diffuse focus.

An initial calibration process may be required for instance to account for differences in natural fluorescence of patients and for the specific characteristics of the ocular analyte sensor employed.

In addition, a standardization may be done measuring the fluorescence intensity of a reference dye, which may have been embedded in the ocular analyte sensor, wherein such a dye is non-active with respect to the analyte.

Whenever the ocular sensor comprises more than one fluorescent label, one could serve as an internal standard in the determination of the analyte concentration in an ocular fluid. An additional calibration may be done by measuring one fluorescent label while exiting another one. This would compensate for the variation (if any) in intensity of the pilot beam when the distance from the eye is slightly varied (order of micrometers).

A calibration table or calibration curve as used herein means a table or curve containing in correlated form fluorescence intensity or fluorescence intensity ratios and their corresponding actual analyte concentrations.

If the analyte is glucose, a calibration table or calibration curve can for instance be obtained once a day or just before testing of blood glucose levels by using at least three standard solutions with known glucose concentrations over a glucose concentration range from 30 to 500 mg/L. The obtained calibration table or curve is preferably stored in the apparatus which is used subsequently to determine blood glucose concentration.

The correlation between blood glucose concentration and ocular glucose concentration can be determined by methods well known in the art. See, for example, March et al., Diabetes Care 5, 259-65, 1982. It is preferred to store such correlation between blood glucose concentration and ocular glucose concentration in the apparatus of the present invention so that the measurement of ocular glucose concentration can be converted into a value of blood glucose concentration.

Standard solutions can be provided to a user in calibration kits. They are stored in containers, preferably in a rectangular container having a plurality of separate compartments. The kits can also include calibration instruction.

Further, the measured blood glucose concentration value may be transmitted to another piece of equipment via wire or cable, or wirelessly, such as via radio frequency or infrared transmission. A telemetry signal can be transmitted to an infusion pump, which can provide insulin to maintain suitable levels of glucose in the body. The telemetry signal may be analog or digital.

Infusion pumps are well known in the art for delivering a selected medication to a patient including humans and other animals in accordance with an administration schedule which can be pre-selected or, in some instances, preprogrammed. Pumps for use in this invention can be worn externally or can be directly implanted into the body of a mammal, including a human, to deliver a specific insulin to the mammal in controlled doses over an extended period of time. Such pumps are well known and are described, for example, in U.S. Pat. Nos. 5,957,890, 4,923,375, 4,573,994, and 3,731,681.

In another aspect, this invention provides a method for measuring an analyte level, preferably a blood glucose level from an ocular fluid. First, an ocular analyte sensor in contact with the ocular fluid is provided; second, providing the fluorescence photometer of the present invention. The photometer is used by looking into an optical window while holding the apparatus in front of the eye.

In order to exactly positioning the apparatus the pilot beam is irradiated into the pupil of the patient's eye and the pupil fluorescence is measured. Once the photometer is exactly positioned the measurement beam is irradiated onto the patient's eye, preferably onto the iris to excite the ocular analyte sensor. Upon irradiation said ocular analyte sensor emits a fluorescence having at least one wavelength band. The detected fluorescence intensity emitted by the sensor is then correlated to the analyte ocular and/or blood concentration.

A suitable ocular sensor is for example an ophthalmic lens comprising an analyte receptor labeled with a first fluorescent label and an analyte competitor labeled with a second fluorescent label. The two fluorescent labels are selected in a way that while the competitor is bound to the receptor, the fluorescence of one of two fluorescent labels is quenched via a fluorescence resonance energy transfer by the other fluorescent label. By monitoring the change of the fluorescence intensity at a wavelength around the peak of the fluorescence of the quenchable fluorescent label, the amount of the fluorescently labeled competitor that is displaced from the receptor by the analyte is measured and provides a means of determining the analyte concentration in an ocular fluid.

Fluorescent labels, such as fluorescein, indocyanine green, malachite green, and rhodamine, which are quenched when the competitor moiety is bound but are unquenched when the competitor moiety is not bound, are preferred for use as quenchable fluorescent label in the ocular glucose sensor. A particularly preferred combination of fluorescent labels is the combination of fluorescein (donor) and rhodamine (acceptor).

The sensitivity of the ocular glucose sensor can be controlled by altering the concentration of the quenchable fluorescent label. Increasing the concentration of the quenchable fluorescent label in the ocular glucose sensor increases the range of fluorescence intensity and thereby increases the sensitivity of resulting measurements.

The glucose receptor moiety comprises one or more binding site for glucose. The binding site also binds a moiety that competes with glucose for binding and is therefore referred to herein as a "glucose/competitor moiety binding site". Binding of both the competitor moiety and glucose to the glucose/competitor moiety binding site is reversible. The receptor moiety can be, for example, antibodies, boronic acid, a genetically engineered bacterial fluoriprotein, or preferably concanavalin A (Mansouri & Schultz, Bio/Tech 2:385 (1984)).

It is well known to a person skilled in the art to select a competitor moiety which will compete with glucose for binding to a glucose/competitor moiety binding site. For example, suitable competitors to glucose for binding to concanavalin A are a polymeric carbohydrate, in particular dextran, or a glycoconjugate as described in U.S. Pat. No. 5,342,789.

A particular preferred receptor competitor system is a system of a labeled concanavalin A and a labeled dextran, especially rhodamine-concanavalin A and fluorescein dextran.

In alternative a suitable ocular analyte sensor may be an ophthalmic lens comprising a protein sensing molecule capable of binding analyte and having the property upon irradiation of emitting a fluorescence light having at least a fluorescence band that changes in intensity or decay time in a concentration-dependent manner when said molecule is bound to the analyte. If the analyte is glucose, preferably the protein is an *E. Coli* glucose binding protein GGBP or functionally equivalent fragments thereof. Proteins other then GGBP may be used, for example, hexokinase, glucokinase, or mutants of hexokinase or mutants of GGBP. For example, it is especially useful to modify the GGBP molecule to include cysteine residues as described in U.S. Pat. No. 6,197,534. In addition the sensing molecule may be labeled with one or more detectable labels like solvent sensitive probes such as dansyl probes, anilinonapthalene probes, deproxyl probes and similar probes which are sensitive to the polarity of the local environment. Other useful probes include donor-acceptor pairs such us fluorescein to rhodamine, coumarin to fluorescein or rhodamine. Still another class of useful label pairs include fluorophore-quencher pairs such as acrylamide groups, iodine and bromate etc in which the second group is a quencher which decreases the fluorescence intensity of the fluorescent group.

A suitable ocular analyte sensor may in addition comprise a reference dye, e.g. for standardization or calibration purposes, which upon irradiation emits a characteristic fluorescence, wherein such a dye is non-active with respct to the analyte.

An ophthalmic lens is, for example, a removable lens, such as a contact lens, or a permanently implanted lens, such as an intraocular lens, a subconjunctival lens, or an intracorneal lens. Permanently implanted lenses are particularly well-suited for use in individuals who have compromised ocular function (e.g., cataracts) and also diabetic disease.

Ophthalmic lenses can be corrective lenses or can be constructed so that they do not affect visual acuity. Contact lenses optionally can comprise a tint and are preferably disposable, which reduces the risk of infection for the user. As used herein, the term "ophthalmic lens" may also refer to a shunt or implant that may rest in the subconjunctival part of the eye.

Ophthalmic lenses according to embodiments of the invention can be worn chronically to provide repeated measurements or can be worn for a single measurement. Both qualitative and quantitative measurements can be performed.

The invention claimed is:

1. A hand-held fluorescence photometer for measuring an analyte level from an ocular fluid comprising:
   (a) at least a first irradiating means for providing a pilot beam when in use, wherein said pilot beam is irradiated onto an eye of a user from outside the cornea of the eye to excite a pupil fluorescence or first fluorescence wherein said pupil fluorescence travels along a first optical path;
   (b) a first detecting means located on the first optical path for detecting the intensity of the pupil fluorescence within a given wavelength range;
   (c) a second irradiating means for providing a measurement beam when in use, wherein said measurement beam is irradiated onto the eye of a user from outside the cornea of the eye to excite an ocular analyte sensor, wherein said ocular analyte sensor is adapted to be in contact with an ocular fluid and wherein said ocular analyte sensor, upon irradiation with said second irradiating means, is adapted to emit a total fluorescence having at least a second fluorescence wavelength band, wherein said second fluorescence travels along a second optical path;
   (d) a second detecting means located on the second optical path for detecting the intensity of the second fluorescence at a given wavelength; wherein, when the fluorescence photometer is in use, said pilot beam is positioned at a fixed angle and distance from the measurement beam wherein said angle is greater than 0 degrees and smaller than 90 degrees; and
   (e) a correlation means for correlating the intensity of the pupil fluorescence to the distance of the fluorescence photometer to the eye and thereby determining an exact position of the fluorescence photometer for a measurement, and only providing said measurement once the exact position has been reached.

2. The fluorescence photometer of claim 1 wherein the fluorescence photometer is adapted to irradiate the measurement beam onto the iris of the user's eye.

3. The fluorescence photometer of claim 1 wherein the pilot beam as well as the measurement beam have confocal optical paths.

4. The fluorescence photometer of claim 1 wherein the analyte is blood glucose.

5. The fluorescence photometer of claim 1 wherein, when the fluorescence photometer is in use, said ocular analyte sensor emits a total fluorescence having second and third wavelength bands upon irradiation with said irradiating means and further comprising:
   (e) an optical path comprising splitting means for splitting said total fluorescence having both bands into the second fluorescence having said second wavelength band and third fluorescence having said third wavelength band, wherein said second fluorescence travels along the second optical path and said third fluorescence travels along a third optical path; and
   (f) a third detecting means located in the third optical path for detecting the intensity of the third fluorescence at a third wavelength.

6. The fluorescence photometer of claim 1 further comprising a third irradiating means wherein the second irradiating means is used to excite the second fluorescence and the third irritating means is used to excite a third fluorescence.

7. The fluorescence photometer of claim 1 further comprising a processing circuit and/or arithmetic means, a display and a power supply.

8. A method to determine an analyte level from an ocular fluid comprising:
   (a) providing an ocular analyte sensor in contact with the ocular fluid;
   (b) providing a hand-held fluorescence photometer in front of a patient's eye, wherein in use said photometer provides a pilot beam and a measurement beam;
   (c) irradiating a pilot beam onto the eye of a user from outside the cornea of the eye to excite a pupil fluorescence or first fluorescence wherein said first fluorescence travels along a first optical path;
   (d) detecting the intensity of the first fluorescence within a given wavelength range;
   (e) correlating the intensity of the pupil fluorescence to the distance of the fluorescence photometer to the eye and thereby determining an exact position of the fluorescence photometer for a measurement; and once the exact position has been reached
   (f) irradiating a measurement beam onto the eye of a user from outside the cornea of the eye to excite the ocular analyte sensor, wherein said ocular analyte sensor emits a total fluorescence having at least a second fluorescence wavelength band upon irradiation with said irradiating means;
   (g) detecting the intensity of the second fluorescence at a given wavelength; and
   (h) correlating said intensity of the second fluorescence to the analyte level.

9. The method of claim 8 wherein, when the fluorescence photometer is in use, said pilot beam is positioned at a fixed angle and distance from the measurement beam wherein said angle is greater than 0 degrees and smaller than 90 degrees.

10. The method of claim 8 wherein the measurement beam is irradiated into the iris of the patient's eye.

11. The method of claim 8 wherein the analyte is blood glucose.

12. The method of claim 8 wherein a processing circuit sends a signal to automatically go from step (f) to (g).

* * * * *